United States Patent
Jackson (12) 
(10) Patent No.: US 7,476,239 B2
(45) Date of Patent: Jan. 13, 2009

(54) POLYAXIAL BONE SCREW WITH COMPOUND ARTICULATION

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 0 days.

(21) Appl. No.: 11/126,965

(22) Filed: May 10, 2005

(65) Prior Publication Data

US 2006/0271047 A1    Nov. 30, 2006

(51) Int. Cl.
*A61B 17/70*    (2006.01)
(52) U.S. Cl. ..................................... 606/266
(58) Field of Classification Search ............... 606/61, 606/69, 72–73, 246, 250–253, 257, 264–270, 606/279, 305, 306
See application file for complete search history.

(56) References Cited

U.S. PATENT DOCUMENTS

| | | |
|---|---|---|
| 4,946,458 A | 8/1990 | Harms et al. |
| 5,129,388 A | 7/1992 | Vignaud et al. |
| 5,207,678 A | 5/1993 | Harms et al. |
| 5,261,912 A | 11/1993 | Frigg |
| 5,312,404 A | 5/1994 | Asher et al. |
| 5,360,431 A | 11/1994 | Puno et al. |
| 5,395,371 A | 3/1995 | Miller et al. |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stevenhagen et al. |
| 5,496,321 A | 3/1996 | Puno et al. |
| 5,554,157 A | 9/1996 | Errico et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,426 A | 3/1997 | Ralph et al. |
| 5,669,911 A | 9/1997 | Errico et al. |
| 5,672,176 A | 9/1997 | Biedermann et al. |
| 5,681,319 A | 10/1997 | Biedermann et al. |
| 5,690,630 A | 11/1997 | Errico et al. |
| 5,716,356 A | 2/1998 | Biedermann et al. |

(Continued)

FOREIGN PATENT DOCUMENTS

DE    G9202745.8    4/1992

(Continued)

OTHER PUBLICATIONS

*EBI Omega 21* Brochure, EBI Spine Systems, pub. 1999.

(Continued)

*Primary Examiner*—Eduardo C Robert
*Assistant Examiner*—Michael J Araj
(74) *Attorney, Agent, or Firm*—John C. McMahon (57)    ABSTRACT

A polyaxial bone screw assembly includes a threaded shank body having an upper capture structure, a receiver and a retainer having spherical inner and outer surfaces. The retainer is compressible, having an opening with two ends that may be pressed toward one another. The retainer spherical surfaces slidingly mate with both the receiver and the capture structure, providing multiple or compound polyaxial articulation.

21 Claims, 4 Drawing Sheets

U.S. PATENT DOCUMENTS

| | | | |
|---|---|---|---|
| 5,725,528 | A | 3/1998 | Errico et al. |
| 5,728,098 | A | 3/1998 | Sherman et al. |
| 5,733,286 | A | 3/1998 | Errico et al. |
| 5,738,685 | A | 4/1998 | Halm et al. |
| 5,782,833 | A | 7/1998 | Haider |
| 5,797,911 | A | 8/1998 | Sherman et al. |
| 5,800,435 | A | 9/1998 | Errico et al. |
| 5,817,094 | A | 10/1998 | Errico et al. |
| 5,863,293 | A | 1/1999 | Richelsoph |
| 5,876,402 | A | 3/1999 | Errico et al. |
| 5,879,350 | A | 3/1999 | Sherman et al. |
| 5,879,351 | A | 3/1999 | Viart |
| 5,882,350 | A | 3/1999 | Ralph et al. |
| 5,885,286 | A | 3/1999 | Sherman et al. |
| 5,891,145 | A * | 4/1999 | Morrison et al. ............... 606/61 |
| 5,954,725 | A | 9/1999 | Sherman et al. |
| 5,961,517 | A | 10/1999 | Biedermann et al. |
| 5,964,760 | A | 10/1999 | Richelsoph |
| 6,010,503 | A | 1/2000 | Richelsoph et al. |
| 6,019,759 | A | 2/2000 | Rogozinski |
| 6,022,350 | A | 2/2000 | Ganem |
| 6,053,917 | A | 4/2000 | Sherman et al. |
| 6,063,090 | A | 5/2000 | Schlapfer |
| 6,074,391 | A | 6/2000 | Metz-Stavenhagen et al. |
| 6,077,262 | A | 6/2000 | Schlapfer et al. |
| 6,086,588 | A | 7/2000 | Ameil et al. |
| 6,090,110 | A | 7/2000 | Metz-Stavenhagen |
| 6,090,111 | A * | 7/2000 | Nichols ....................... 606/61 |
| 6,099,528 | A | 8/2000 | Saurat |
| 6,110,172 | A | 8/2000 | Jackson |
| 6,113,601 | A * | 9/2000 | Tatar ............................ 606/61 |
| 6,132,431 | A | 10/2000 | Nilsson et al. |
| 6,132,432 | A | 10/2000 | Richelsoph |
| 6,132,434 | A | 10/2000 | Sherman et al. |
| 6,146,383 | A | 11/2000 | Studer et al. |
| 6,187,005 | B1 | 2/2001 | Brace et al. |
| RE37,161 | E | 5/2001 | Michelson et al. |
| 6,224,596 | B1 | 5/2001 | Jackson |
| 6,248,105 | B1 | 6/2001 | Schlapfer et al. |
| 6,254,602 | B1 | 7/2001 | Justis |
| 6,273,888 | B1 | 8/2001 | Justis |
| 6,280,442 | B1 | 8/2001 | Barker et al. |
| 6,280,445 | B1 | 8/2001 | Morrison et al. |
| 6,287,308 | B1 | 9/2001 | Betz et al. |
| 6,287,311 | B1 | 9/2001 | Sherman et al. |
| 6,302,888 | B1 | 10/2001 | Mellinger et al. |
| 6,309,391 | B1 | 10/2001 | Crandall et al. |
| 6,355,040 | B1 | 3/2002 | Richelsoph et al. |
| 6,361,535 | B2 * | 3/2002 | Jackson ....................... 606/61 |
| RE37,665 | E | 4/2002 | Ralph et al. |
| 6,368,321 | B1 | 4/2002 | Jackson |
| 6,440,137 | B1 | 8/2002 | Horvath et al. |
| 6,471,705 | B1 | 10/2002 | Biedermann et al. |
| 6,485,494 | B1 | 11/2002 | Haider |
| 6,488,681 | B2 | 12/2002 | Martin et al. |
| 6,508,818 | B2 | 1/2003 | Steiner et al. |
| 6,554,834 | B1 | 4/2003 | Crozet et al. |
| 6,558,387 | B2 | 5/2003 | Errico et al. |
| 6,562,040 | B1 | 5/2003 | Wagner |
| 6,565,565 | B1 | 5/2003 | Yuan et al. |
| 6,565,567 | B1 | 5/2003 | Haider |
| 6,582,436 | B2 | 6/2003 | Schlapfer et al. |
| 6,595,992 | B1 | 7/2003 | Wagner et al. |
| 6,613,050 | B1 | 9/2003 | Wagner et al. |
| 6,623,485 | B2 | 9/2003 | Doubler et al. |
| 6,660,004 | B2 * | 12/2003 | Barker et al. ................... 606/61 |
| 6,663,632 | B1 | 12/2003 | Frigg |
| 6,663,635 | B2 | 12/2003 | Frigg et al. |
| 6,689,133 | B2 | 2/2004 | Morrison et al. |
| 6,695,843 | B2 | 2/2004 | Biedermann et al. |
| 6,699,249 | B2 | 3/2004 | Schlapfer et al. |
| 6,716,214 | B1 * | 4/2004 | Jackson ....................... 606/61 |
| 6,723,100 | B2 | 4/2004 | Biedermann et al. |
| 6,733,502 | B2 | 5/2004 | Altarac et al. |
| 6,736,816 | B2 | 5/2004 | Ritland |
| 6,755,829 | B1 | 6/2004 | Bono et al. |
| 6,770,075 | B2 | 8/2004 | Howland |
| 6,780,186 | B2 | 8/2004 | Errico et al. |
| 6,827,719 | B2 | 12/2004 | Ralph et al. |
| 6,835,196 | B2 | 12/2004 | Biedermann et al. |
| 6,840,940 | B2 | 1/2005 | Ralph et al. |
| 6,858,031 | B2 | 2/2005 | Morrison et al. |
| 6,896,677 | B1 * | 5/2005 | Lin ............................ 606/61 |
| 2001/0001119 | A1 | 5/2001 | Lombardo |
| 2002/0026193 | A1 * | 2/2002 | Barker et al. ................... 606/61 |
| 2002/0087161 | A1 * | 7/2002 | Randall et al. ................. 606/61 |
| 2002/0143341 | A1 * | 10/2002 | Biedermann et al. .......... 606/73 |
| 2003/0004512 | A1 * | 1/2003 | Farris et al. ................... 606/61 |
| 2005/0049588 | A1 * | 3/2005 | Jackson ....................... 606/61 |

FOREIGN PATENT DOCUMENTS

| | | |
|---|---|---|
| DE | 19507141 | 9/1996 |
| EP | 1121902 | 8/2001 |

OTHER PUBLICATIONS

*Claris Instumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica SpineTech, no publish date.
*SDRS Surgical Dynamics Rod System* Brochure, Surgical Dynamics, pub. 1998-99.
*Versalok Low Back Fixation System* Brochure, Wright Medical Technology, Inc., pub. 1997.
*The Strength of Innovation Advertisement*, Blackstone Medical Inc., no publish date.
*The Moss Miami 6. Omm System* Advertisement, author unknown, no publish date.

\* cited by examiner

POLYAXIAL BONE SCREW WITH COMPOUND ARTICULATION

BACKGROUND OF THE INVENTION

The present invention is directed to polyaxial bone screws for use in bone surgery, particularly spinal surgery. Such screws have a rod receiver that can swivel about a shank of the bone screw, allowing the receiver to be positioned in any of a number of angular configurations relative to the shank.

Many spinal surgery procedures require securing various implants to bone and especially to vertebrae along the spine. For example, elongate rods are often utilized that extend along the spine to provide support to vertebrae that have been damaged or weakened due to injury or disease. Such rods must be supported by certain vertebrae and support other vertebrae.

The most common mechanism for providing vertebral support is to implant bone screws into certain bones which then in turn support the rod or are supported by the rod. Bone screws of this type may have a fixed head or receiver relative to a shank thereof. In the fixed bone screws, the receiver cannot be moved relative to the shank and the rod must be favorably positioned in order for it to be placed within the receiver. This is sometimes very difficult or impossible to do. Therefore, polyaxial bone screws are commonly preferred.

Polyaxial bone screws allow rotation of the receiver about the shank until a desired rotational position of the receiver is achieved relative to the shank. Thereafter, a rod can be inserted into the receiver and eventually the receiver is locked or fixed in a particular position relative to the shank.

A variety of polyaxial or swivel-head bone screw assemblies are available. One type of bone screw assembly includes an open receiver that allows for placement of a rod within the receiver. A closure top or plug is then used to capture the rod in the receiver of the screw.

Because such implants are for placement within the human body, it is desirable for the implant to have as little effect on the body as possible. Consequently, heavy, bulky implants are undesirable and lighter implants with a relatively small profile both in height and width are more desirable. However, a drawback to smaller, lighter implants is that they may be more difficult to rigidly fix to each other and into a desired angular position. Lack of bulk may also mean lack of strength, resulting in slippage under high loading. Also, more component parts may be required to rigidly fix the implant in a desired position. A further drawback of smaller components is that they may be difficult to handle during surgery because of their small size or fail to provide adequate driving or gripping surfaces for tools used to drive the shank into bone or drive the closure top into the screw head.

SUMMARY OF THE INVENTION

A polyaxial bone screw assembly of the present invention includes a shank having a body for fixation to a bone and an upper portion or capture structure. The shank upper portion is receivable in a receiver having a cavity. A retainer, preferably a collar-like retaining and articulating structure is also receivable in the cavity. A first polyaxial articulation is formed by the shank upper portion and the retainer and a second polyaxial articulation is formed by the retainer and the receiver. Specifically, the shank upper portion has a convex surface and the retainer has an inner concave surface in slidable mating engagement with the convex surface. The retainer also has an outer convex surface and the receiver has an inner concave surface in slidable mating engagement with the retainer convex surface. Thus, cooperation between the retainer and the shank upper portion at one side thereof and the receiver at the other side thereof allows for multiple or compound articulation.

In an illustrated embodiment, the concave and convex surfaces of the shank upper portion, the retainer and the receiver are all substantially spheroidal, thus providing two spheroidal or ball-and-socket joints. These spheroidal surfaces may further include a roughening or high friction surface finish to enhance frictional engagement when a compressive force is placed on the shank upper portion, resulting in fixed frictional engagement between the shank upper portion, the retainer and the receiver.

In addition to having an inner concave seating surface and an outer convex surface, the illustrated retainer is resilient and open. The illustrated retainer includes first and second spaced ends and is compressible and expandable with the first and second ends being movable toward and away from one another. The retainer may be sized and shaped to be top or bottom loadable into the receiver. In a preferred embodiment and method of assembly, the resilient and open retainer is sized and shaped to be expandable about a neck of a bone screw shank and then compressible about the shank neck. The shank neck is disposed between the shank upper portion and the shank body. The shank upper portion, with the compressed retainer disposed about the shank neck may then be inserted through a bottom opening of the receiver. Upon expanding to an original form, the retainer and the shank upper portion are captured within a cavity of the receiver. The retainer is then expanded and moved upwardly to a position surrounding the shank upper portion. Upon recovery to the original shape, the retainer completely captures the shank upper portion within the receiver and is in sliding engagement with both the convex surface of the upper portion and the inner concave surface of the receiver. The shank upper portion is encircled by the retainer and held in spaced relation with the receiver. The convex surface of the shank upper portion thus does not contact any surface defining the receiver cavity.

Another aspect of the invention is a tool engagement formation on the shank upper portion, allowing for non-slip engagement by a tool for driving the bone screw shank into bone. Furthermore, the illustrated receiver includes an open channel communicating with the cavity that receives the shank upper portion and the retainer. The channel is sized and shaped for receiving a rod or other structural member and includes arms with a discontinuous guide and advancement structure for mating with a guide and advancement structure of a closure structure. The guide and advancement structure is preferably a flange form or other non-splaying guide and advancement structure. The shank upper portion is sized and shaped for frictional contact with a rod seated in the channel. In operation, the closure structure operably urges the rod into direct contact with the upper portion of the bone screw shank which in turn frictionally engages the shank upper portion, the retainer and the receiver, fixing the bone screw shank body in a selected angular orientation with respect to the receiver.

OBJECTS AND ADVANTAGES OF THE INVENTION

Therefore, objects of the present invention include providing a polyaxial bone screw assembly with features that may be readily, securely fastened to each other and to bone. A further object of the invention is to provide a polyaxial bone screw assembly with increased angular articulation. Furthermore, it is an object of the invention to provide a lightweight, low profile polyaxial bone screw assembly that may be assembled prior to implantation and also assembles in such a manner that the components cooperate to create an overall structure that prevents unintentional disassembly. Another object of the invention is to provide a polyaxial bone screw assembly that is relatively easy to use, inexpensive to produce and especially well adapted for the intended usage thereof.

Other objects and advantages of the invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

With reference to FIGS. 1-12, the reference numeral 1 generally represents a polyaxial bone screw assembly according to the present invention. The assembly 1 includes a shank 4 that further includes a body 6 integral with an upwardly extending capture structure 8; a receiver 10; and an independent retainer illustrated as an open collar-like retaining and articulating structure 12. The shank 4, the receiver 10 and the retaining and articulating structure 12 preferably are assembled prior to implantation of the shank body 6 into a vertebra 15.

Figure 1:
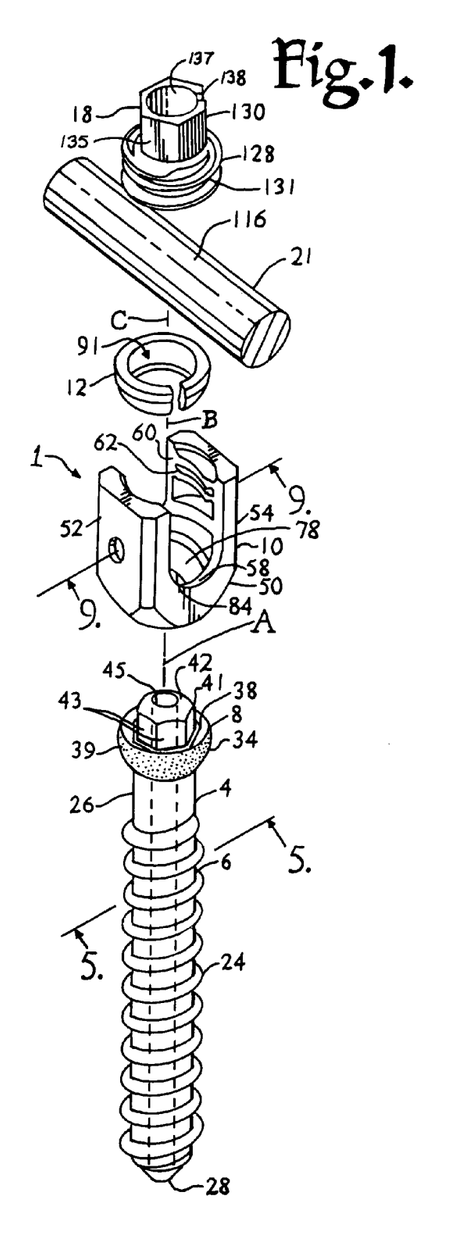
FIG. 1 is an exploded perspective view of a polyaxial bone screw assembly according to the present invention having a shank with a capture structure at one end thereof, a receiver, and a retaining and articulating structure, and shown with a rod and a closure structure.

FIG. 1 further shows a closure structure 18 for compressing and biasing a longitudinal member such as a rod 21 against the capture structure 8 which biases the retaining and articulating structure 12 into fixed frictional contact with both the capture structure 8 and the receiver 10, so as to fix the rod 21 relative to the vertebra 15. The receiver 10, the retaining and articulating structure 12 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near an end of an implantation procedure.

Figure 5:
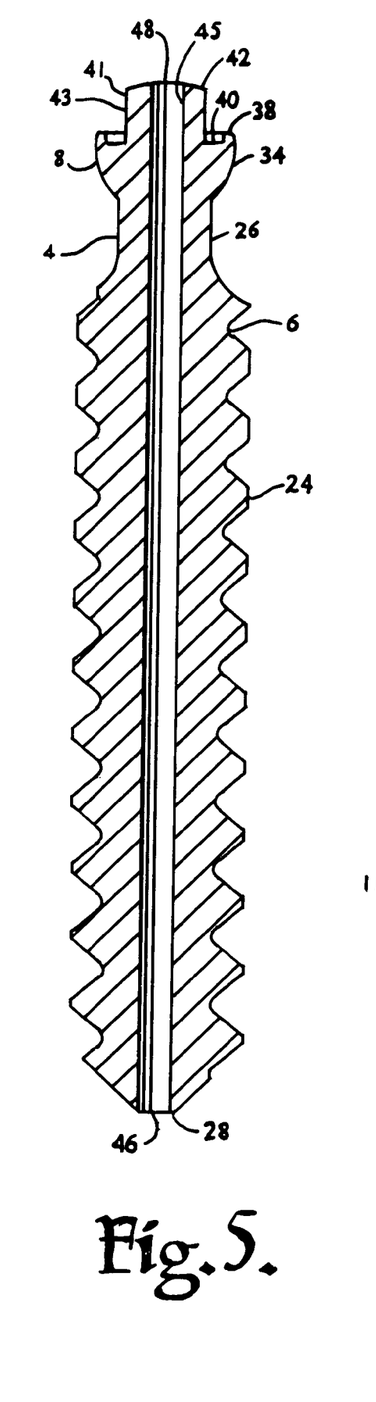
FIG. 5 is an enlarged cross-sectional view of the bone screw shank and capture structure, taken along the line 5-5 of FIG. 1.
Figures 8, 9, 11:
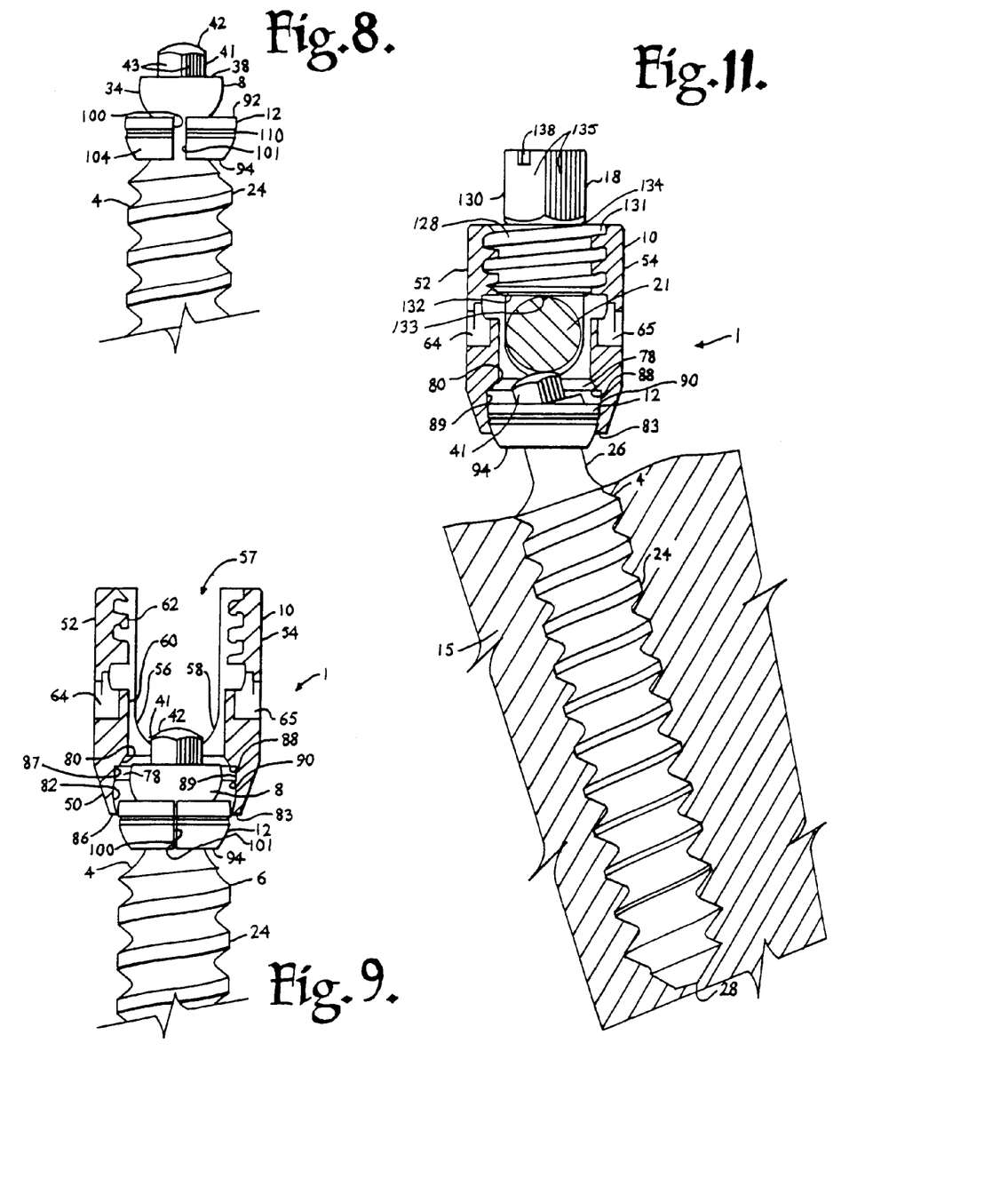
FIG. 8 is an enlarged and fragmentary front elevational view, similar to FIG. 7, showing the bone screw shank and the retaining and articulating structure in a first stage of assembly.
FIG. 9 is an enlarged and fragmentary front elevational view of the shank and the retaining and articulating structure similar to FIG. 8, and further showing the receiver in cross-section along the line 9-9 of FIG. 1 and in an intermediate stage of assembly with the shank and retaining and articulating structure.
FIG. 11 is an enlarged front elevational view of the bone screw shank and retaining and articulating structure of FIG. 9 shown fully assembled with the receiver shown in cross-section, and further shown assembled with the rod of FIG. 1 in cross-section and the closure structure of FIG. 1 in front elevation, the shank further shown implanted in a vertebra.

The shank 4, best illustrated in FIGS. 1 and 5, is elongate, with the shank body 6 having a helically wound bone implantable thread 24 extending from near a neck 26 located adjacent to the capture structure 8 to a tip 28 of the body 6 and extending radially outwardly therefrom. During use, the body 6 utilizing the thread 24 for gripping and advancement is implanted into the vertebra 15 leading with the tip 28 and driven down into the vertebra 15 with an installation or driving tool (not shown), so as to be implanted in the vertebra 15 to near the neck 26, as shown in FIG. 11, and as is described more fully in the paragraphs below. The shank 4 has an elongate axis of rotation generally identified by the reference letter A. It is noted that any reference to the words top, bottom, up and down, and the like, in this application refers to the alignment shown in the various drawings, as well as the normal connotations applied to such devices, and is not intended to restrict positioning of the assembly 1 in actual use.

The neck 26 extends axially outwardly and upwardly from the shank body 6. With particular reference to FIG. 5, the illustrated neck 26 is of reduced radius as compared to the shank body 6 and an outer diameter of the thread 24. Further extending axially and outwardly from the neck 26 is the shank upper portion or capture structure 8 that provides a connective or capture apparatus disposed at a distance from the thread 24 and thus at a distance from the vertebra 15 when the body 6 is implanted in the vertebra 15.

Figure 6:
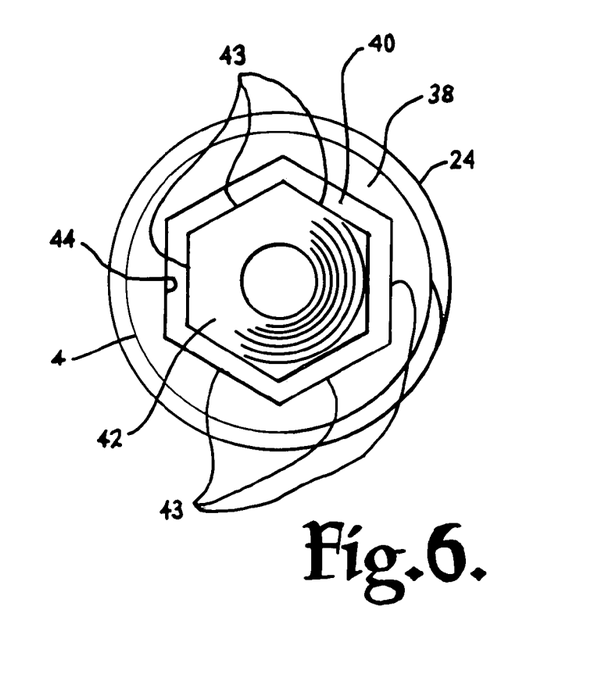
FIG. 6 is an enlarged top plan view of the bone screw shank and capture structure of FIG. 5.

The capture structure 8 is configured for connecting the shank 4 to the receiver 10 and capturing the shank 4 in the receiver 10. With particular reference to FIGS. 5 and 6, the capture structure 8 has an outer, convex and substantially spherical surface 34 that extends outwardly and upwardly from the neck 26 and terminates at a substantially annular surface 38. The spherical surface 34 has an outer radius configured for sliding cooperation and ultimate frictional mating with a concave surface of the retaining and articulating structure 12 having a substantially similar radius, discussed more fully in the paragraphs below. The flat surface 38 is substantially perpendicular to the axis A. With particular reference to FIG. 1, the spherical surface 34 shown in the present embodiment includes a roughened or textured surface or surface finish 39, or may be scored, knurled, or the like, for enhancing frictional engagement with the retaining and articulating structure 12, discussed more fully below. It is foreseen, however, that the surface 34 may be smooth in other embodiments. A counter sunk substantially planar base or seating surface 40 also is disposed perpendicular to the axis A and extends radially from a centrally located tool engagement structure 41. The sunken seating surface 40 is disposed between the tool engagement structure and the surface 34. The structure 41 has a top 42 and six driving faces 43 that form a hexagonal extension head driving structure mateable with a socket driving tool (not shown). The base 40 also includes a hexagonal outer perimeter 44 defined by outer driving faces that are parallel to the axis A and terminate at the surface 38. The tool engagement structure 41 is coaxial with the bone screw body 6 and extends along the axis A. In operation, a driving tool (not shown) fits about and engages the tool engagement structure 41 at the faces 43 for both driving and rotating the shank body 6 into the vertebra 15. A bottom of the driving tool may abut against the base 40 and also the faces defining the outer hexagonal perimeter 44, providing additional surfaces for engagement with the driving tool. It is foreseen that in other embodiments according to the invention, in particular smaller embodiments, a curved, concave surface may extend from the tool engagement structure 41 to the outer spherical surface 34, allowing for the tool engagement structure 41 to be designed with a somewhat longer axial length and thus providing a greater surface area for engagement with a driving tool, but without the planar seating surface 42 and additional planar driving faces because of the limitation of the small size of such a bone screw.

It is also foreseen that in some embodiments, the bone screw shank upper portion may have an internal drive or imprint rather than the external tool engagement structure 41. Such an internal drive may, for example, be an aperture having a hex shape and designed to receive a hex tool of an Allen wrench type, into the aperture for rotating and driving the bone screw shank 4. Such a tool engagement structure may take a variety of tool-engaging forms and may include one or more apertures of various shapes, such as a pair of spaced apart apertures or a multi-lobular aperture, such as those sold under the trademark TORX, or the like.

Figures 10, 12:
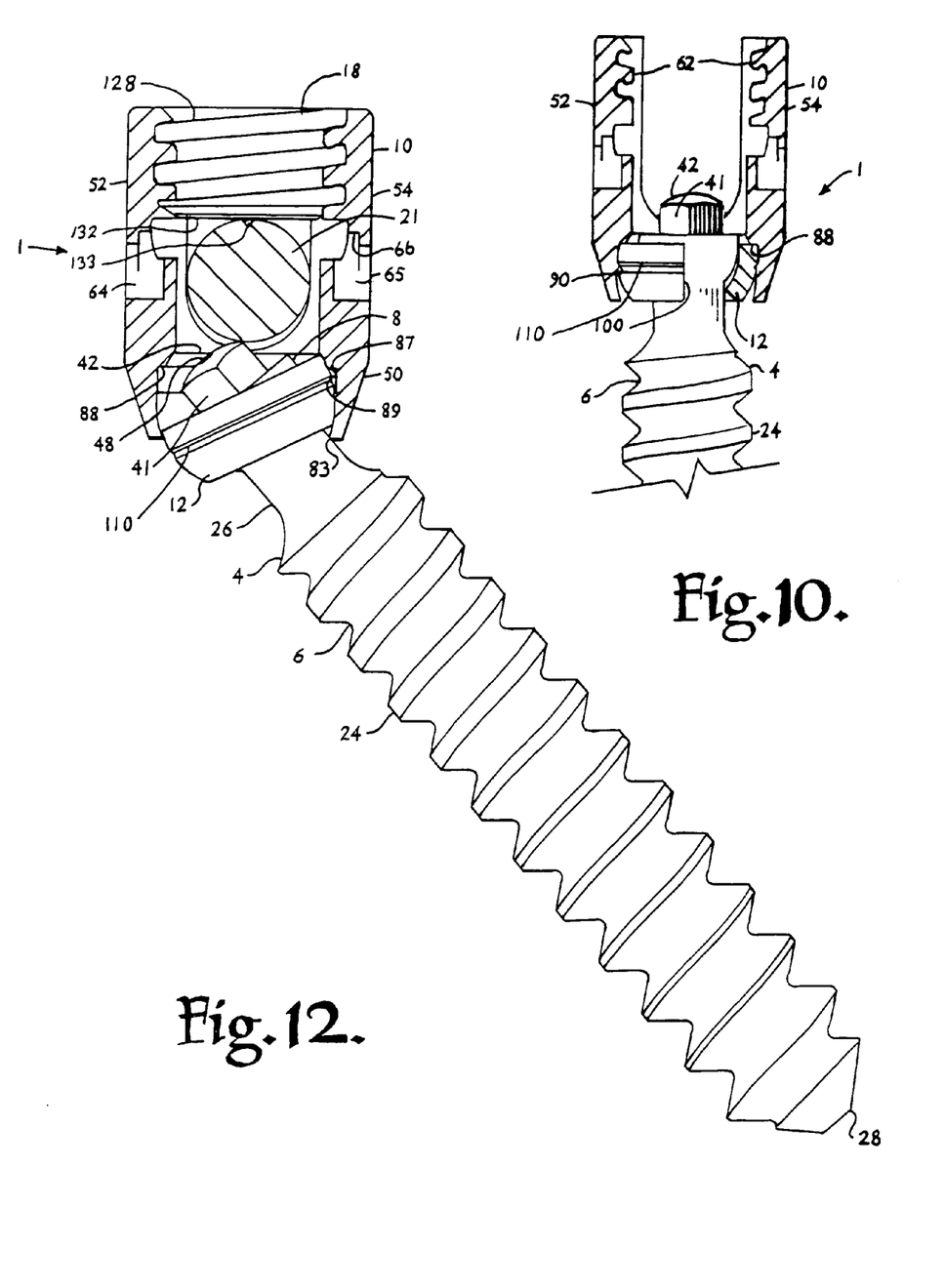
FIG. 10 is an enlarged and fragmentary front elevational view of the shank and the retaining and articulating structure similar to FIG. 9, with portions broken away to shown the detail thereof, and the receiver shown in cross-section, illustrating a final stage of assembly of the shank capture structure with the retaining and articulating structure.
FIG. 12 is an enlarged partially front elevational and partially cross-sectional view of the bone screw assembly, rod and closure structure, similar to FIG. 10, illustrating another possible angular orientation of the bone screw shank with respect to the receiver.

The top end surface 42 of the shank 4 is preferably curved or dome-shaped as shown in the drawings, for simple smooth contact engagement or positive mating engagement with the rod 21, when the bone screw assembly 1 is assembled, as shown in FIGS. 11 and 12 and in any alignment of the shank 4 relative to the receiver 10. In certain embodiments, the surface 42 is smooth. While not required in accordance with the practice of the invention, the surface 42 may be scored, knurled or the like to further increase frictional positive mating engagement between the surface 42 and the rod 21.

The shank 4 shown in the drawings is cannulated, having a small central bore 45 extending an entire length of the shank 4 along the axis A, coaxial with the threaded body 6. The bore 45 has a first circular opening 46 at the shank tip 28 and a second circular opening 48 at the top surface 42. The bore 45 provides a passage through the shank 4 interior for a length of wire (not shown) inserted into the vertebra 15 prior to the insertion of the shank body 6, the wire providing a guide for insertion of the shank body 6 into the vertebra 15.

Referring to FIGS. 1 and 9 through 12, the receiver 10 has a generally U-shaped appearance with a discontinuous partially cylindrical inner profile and a faceted outer profile. The receiver 10 includes a base 50 integral with a pair of upstanding arms 52 and 54 forming a U-shaped cradle and defining a U-shaped channel 56 between the arms 52 and 54 with an upper opening 57 and a lower seat 58 having substantially the same radius as the rod 21 for operably snugly receiving the rod 21.

Each of the arms 52 and 54 has an interior surface 60 that defines the inner cylindrical profile and includes a partial helically wound guide and advancement structure 62. In the illustrated embodiment, the guide and advancement structure 62 is a partial helically wound interlocking flangeform configured to mate under rotation with a similar structure on the closure structure 18, as described more fully below. However, it is foreseen that the guide and advancement structure 62 could alternatively be a V-shaped thread, a buttress thread, a reverse angle thread or other thread like or non-thread like helically wound discontinuous advancement structure for operably guiding under rotation and advancing the closure structure 18 downward between the arms 52 and 54, as well as eventual torquing when the closure structure 18 abuts against the rod 21.

Tool engaging apertures or grip bores 64 and 65 are formed within the arms 52 and 54, respectively which may be used for holding the receiver 10 during assembly with the shank 4 and the retaining and articulating structure 12 and also during the implantation of the shank body 6 into a vertebra 15. A holding tool (not shown) and the apertures 64 and 65 can be configured for a snap on/spring off, twist on/twist off, or other flexible engagement wherein the holding tool has flexible legs which splay outwardly to position the tool for engagement in the apertures 64 and 65. It is noted that the apertures 64 and 65 and the cooperating holding tool may be configured to be of a variety of sizes and locations along any of the surfaces of the arms 52 and 54. In the illustrated embodiment, the apertures 64 and 65 may communicate with upwardly projecting hidden recesses 66 to further aid in securely holding the receiver 10 to a holding tool.

Communicating with and located beneath the U-shaped channel 56 of the receiver 10 is a chamber or cavity 78 substantially defined by an inner surface 80 of the base 50. The cavity 78 opens upwardly into the U-shaped channel 56. The inner surface 80 is substantially spherical, with at least a portion thereof forming a partial internal spherical seating surface 82. The surface 82 is sized and shaped for slidable mating and eventual frictional engagement with the retaining and articulating structure 12, as described more fully below.

The base 50 of the receiver 10 includes a restrictive neck 83, having a radius and defining a bore 84 communicating with the cavity 78 and a lower exterior 86 of the base 50. The bore 84 is coaxially aligned with respect to the rotational axis B of the receiver 10. The neck 83 and the associated bore 84 are sized and shaped to be smaller than an outer radial dimension of the open, uncompressed retaining and articulating structure 12, as will be discussed further below, so as to form a restriction at the location of the neck 83 relative to the retaining and articulating structure 12, to prevent the uncompressed retainer structure 12 from passing from the cavity 78 and out into the lower exterior 86 of the receiver 10 when the retaining and articulating structure 12 is seated and loaded.

Formed in an upper portion of the inner surface 80 that defines the cavity 78 is a circumferentially extending relief 87 defined by an upper annular wall or surface 88 disposed perpendicular to the axis B and a substantially cylindrical wall or side surface 89 coaxial with the axis B. The cylindrical wall 89 extends from the upper surface 88 to the inner seating surface 82. A circumferential ridge 90 is formed at the intersection of the wall 89 and the seating surface 82. As will be described in greater detail with respect to the retaining and articulating structure 12, and as shown in FIG. 10, the circumferential relief 87 provides additional concavity for clearance to allow for expansion of the retaining and articulating structure 12 about the capture structure 8 during initial assembly of the structures 8 and 12 within the receiver 10.

The partially spherical and discontinuous or open retaining and articulating structure or collar 12 is used to retain the capture structure 8 of the shank 4 within the receiver 10 and is also independently slidably and pivotally engageable with both the capture structure 8 and the receiver 10. The retaining and articulating structure 12, best illustrated by FIGS. 1-4, has an operational central axis C that may be the same or different from the axis A associated with the shank 4, or the axis B associated with the receiver 10 when the capture structure 8 and the retaining and articulating structure 12 are installed within the receiver 10. The retaining and articulating structure 12 has a central channel or hollow 91 that passes entirely through the structure 12 from a top surface 92 to a bottom surface 94 thereof. Surfaces that define the channel 91 include a discontinuous inner spherical surface 95 adjacent the top surface 92; an inwardly sloping or partially conical discontinuous surface 96 adjacent the spherical surface 95 and extending toward the axis C; a discontinuous cylindrical wall or surface 97 adjacent the sloping surface 96 coaxial with the axis C; and a discontinuous surface or bevel 98 sloping away from the axis C, adjacent the cylindrical surface 97 and terminating at the bottom surface 94. The spherical surface 95 has a radius sized and shaped to cooperate with a radius of the substantially spherical surface 34 of the capture structure 8 such that the surface 95 slidingly and pivotally mates with the spherical surface 34 as described more fully below. The surface 95 shown in the present embodiment includes a roughening or surface finish 99, similar to the surface treatment 39 on the surface 34 of the capture structure 8. The surface finish 99 is to aid in frictional contact between the surface 95 and the surface 34, once a desired angle of articulation of the shank 4 with respect to the retaining and articulating structure 12 is reached. It is foreseen that in other embodiments according to the invention, the surface 95 may be smooth or have other kinds of surface finish.

Figure 2:
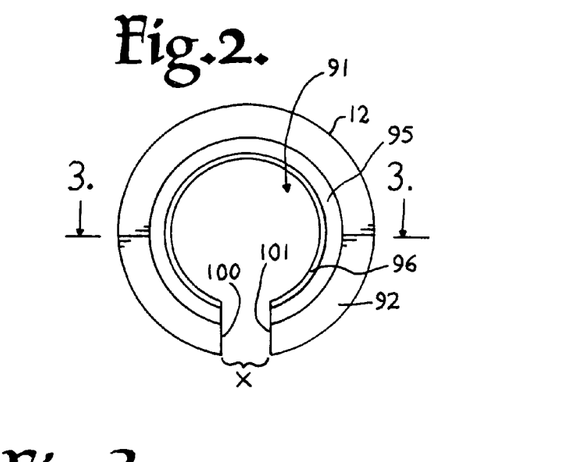
FIG. 2 is an enlarged top plan view of the retaining and articulating structure of FIG. 1.
Figure 3:
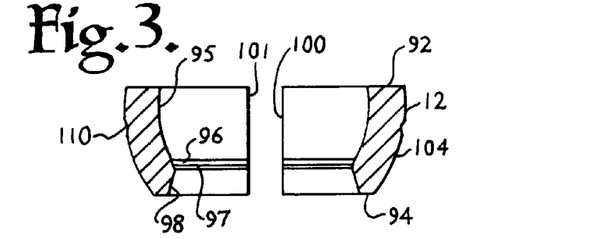
FIG. 3 is a cross-sectional view taken along the line 3-3 of FIG. 2.
Figure 4:
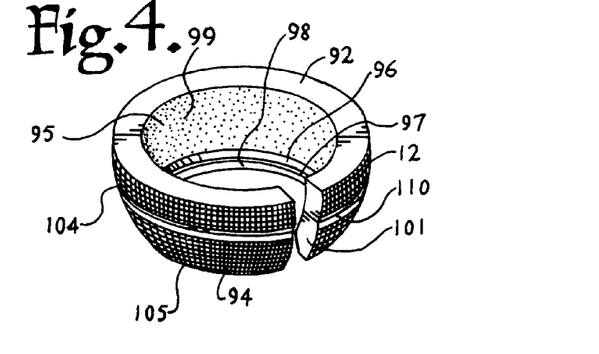
FIG. 4 is an enlarged perspective view of the retaining and articulating structure of FIG. 1.

The resilient retaining and articulating structure 12 includes first and second end surfaces, 100 and 101 disposed in spaced relation to one another and a radially outer partially spherically shaped surface 104. Both end surfaces 100 and 101 are disposed substantially perpendicular to the top surface 92 and the bottom surface 94. A width X between the surfaces 100 and 101 is determined by a desired amount of compressibility of the open retainer structure 12 when loaded on the capture structure 8 and into the receiver 10. The space X shown in FIG. 2 provides adequate space between the surfaces 100 and 101 for the retaining and articulating structure to be pinched, with the surfaces 100 and 101 compressed toward one another as shown in FIG. 9 to an almost touching (as shown in FIG. 9) or touching configuration, to an extent that the compressed retaining and articulating structure 12 is up or bottom loadable into the receiver cavity 78 through the bore 84 defined by the restrictive neck 83 while mounted on the neck 26 of the bone screw shank 6. After passing through the bore 84 simultaneously with the shank upper portion, the retaining and articulating structure 12 expands or springs back to an original uncompressed, rounded or collar-like configuration of FIGS. 11 and 12, once in the cavity 78. FIG. 10 illustrates the structure 12 in a temporary expanded position for sliding over and about the spherical surface 34 of the capture structure 8 until the surfaces 34 and 95 are in slidable mating engagement as shown in FIGS. 11 and 12. Once the resilient structure 12 returns to an original form, but now surrounding the structure 8, the engaged structures 8 and 12 are then movable together within the cavity 78 to a variety of positions in which the surface 104 of the structure 12 is in slidable mating engagement with the seating surface 82 of the receiver 10. It is foreseen that in other embodiments, the retaining and articulating structure 12 may be modified somewhat to being a retaining structure that, when fully installed, is stationery or fixed with respect to the receiver 10, and thus does not swivel or slide with respect to the receiver 10, but does have an articulating or swiveling relationship with an upper portion of the bone screw shank wherein the bone screw upper portion is slidable with respect to the retaining structure.

The embodiment shown in FIG. 2 illustrates the surfaces 100 and 101 as substantially parallel and vertical, however, it is foreseen that it may be desirable to orient the surfaces obliquely or at a slight angle depending upon the amount of compression desired during loading of the retaining and articulating structure 12 into the receiver 10. Also, other embodiments according to the invention, particularly smaller bone screw assemblies, may include retaining and articulating structures small enough to top load into the receiver channel upper opening 57, rather than loading through the receiver neck 83 as will be described in the paragraphs below with respect to the assembly 1.

As indicated in the previous paragraph, the spherically shaped surface 104 of the retaining and articulating structure 12 is sized and shaped to mate with the spherical seating surface 82 of the receiver and has an outer radius approximately equal to the inner radius associated with the surface 82. The retaining and articulating structure outer radius is larger than the radius of the neck 83 of the receiver 10. The outer partially spherically shaped surface 104 includes a high friction surface finish or treatment, such as the knurled surface 105 shown in FIG. 4, or the like. It is foreseen that in other embodiments according to the invention the surface 104 may be smooth.

A discontinuous circumferential V-shaped furrow 110 extends about the surface 104, spaced between the top 92 and bottom 94 surfaces of the structure 12. The furrow 110 runs substantially parallel to both the top and bottom surfaces 92 and 94 and is positioned closer to the top surface 92 than the bottom surface 94. The furrow 110 is sized and shaped to receive the ridge 90 formed between the relief 87 and the seating surface 82 of the receiver 10. With reference to FIG. 10, as the structure 12 expands to receive the capture structure 8 in the cavity 78, the ridge 90 does not hinder such expansion because the furrow 110 receives the ridge 90. Thus, the furrow 110 of the structure 12 in combination with the relief 87 of the receiver 10 work in concert to provide adequate clearance for the installation of the capture structure 8 into the retaining and articulating structure 12 within the cavity 78 of the receiver 10.

The elongate rod or longitudinal member 21 that is utilized with the assembly 1 can be any of a variety of implants utilized in reconstructive spinal surgery, but is normally a cylindrical elongate structure having a smooth cylindrical surface 116 of uniform diameter. The rod 21 is preferably sized and shaped to snugly seat near the bottom of the U-shaped channel 56 of the receiver 10 and, during normal operation, is positioned slightly above the bottom of the channel 56 at the lower seat 58. In particular, the rod 21 normally directly or abutingly engages the shank top surface 42, as shown in FIGS. 11 and 12 and is biased against the domed shank top surface 42, consequently biasing the shank 4 downwardly in a direction toward the base 50 of the receiver 10 when the assembly 1 is fully assembled. For this to occur, the shank top surface 42 must extend at least slightly into the space of the channel 56 when the retaining and articulating structure 12 is snugly seated in the lower part of the receiver cavity 80. The shank 4 and the retaining and articulating structure 12 are thereby locked or held in position relative to the receiver 10 by the rod 21 firmly pushing downward on the shank top surface 42.

With reference to FIGS. 1, 11 and 12, the closure structure or closure top 18 can be any of a variety of different types of closure structures for use in conjunction with the present invention with suitable mating structure on the upstanding arms 52 and 54. In the embodiment shown, the closure top 18 is rotatably received between the spaced arms 52 and 54. It is foreseen that a mating and advancement structure could be located on the external surfaces of the arms 52 and 54 for mating with a closure top.

The illustrated closure top 18 has a generally cylindrical shaped base 128 with an upwardly extending break-off head 130. The base 128 includes a helically wound guide and advancement structure 131 that is sized, shaped and positioned so as to engage the guide and advancement structure 62 on the arms 52 and 54 to provide for rotating advancement of the closure structure 18 into the receiver 10 when rotated clockwise and, in particular, to cover the top or upwardly open portion 57 of the U-shaped channel 56 to capture the rod 21, preferably without splaying of the arms 52 and 54. The base 128 has a lower or bottom surface 132 with a centrally located pointed projection 133 for engaging and penetrating the rod 21 at the rod surface 116. In certain embodiments according to the invention, a circumferential rim (not shown) may also extend from the bottom surface 132, the rim providing additional engagement points with the rod surface 116. The closure structure 18 operably biases against the rod 21 by advancement and applies pressure to the rod 21 under torquing, so that the rod 21 is urged downwardly against the shank top end surface 42 that extends into the channel 56. Downward biasing of the shank top surface 42 operably produces a frictional engagement between the rod 21 and the surface 42 and also urges the capture structure 8 toward the retaining and articulating structure 12 and, in turn, the structure 12 toward the base 50 of the receiver 10, so as to frictionally seat the spherical surface 34 of the capture structure 8 in the inner spherical surface 95 of the retaining and articulating structure 12 and seat the retaining and articulating structure external spherical surface 104 fixedly against the internal spherical seating surface 82 of the receiver 10, also fixing the shank 4 and the retaining and articulating structure 12 in a selected, rigid position relative to the receiver 10. At this time it is also possible for the retaining and articulating structure 12 to expand somewhat for an even tighter fit in the receiver cavity.

The closure structure break-off head 130 is secured to the base 128 at a neck 134 that is sized and shaped so as to break away at a preselected torque that is designed to properly seat the retaining and articulating structure 12 in the receiver 10. The break-off head 130 includes an external faceted surface 135 that is sized and shaped to receive a conventional mating socket type head of a driving tool (not shown) to rotate and torque the closure structure 18. The break-off head 130 also includes a central bore 137 and at least one groove 138 for operably receiving manipulating tools. Alternatively, a closure structure for use with the assembly 1 may not include a break-off head, but rather simply have a cylindrical body with a guide and advancement structure thereon and a top surface with an internal tool engagement structure formed therein, such as a hex aperture or a variety of internal tool-engaging forms of various shapes, such as a multi-lobular aperture sold under the trademark TORX, or the like.

The illustrated closure structure 18 also includes an internal drive removal tool engagement structure (not shown) that may be in the form of an axially aligned aperture, for example, having a hex shape, disposed in the base 128. Such an aperture is accessible after the break-off head 130 breaks away from the base 128. Such an aperture may also be coaxial with the helically wound guide and advancement structure 131 and designed to receive a hex tool, of an Allen wrench type, into the aperture for rotating the closure structure base 128 subsequent to installation so as to provide for removal thereof, if necessary. Such a tool engagement structure may take a variety of tool-engaging forms and may include one or more apertures of various shapes, such as a pair of spaced apart apertures, or a left hand threaded bore, or an easyout engageable step down bore, or a multi-lobular aperture, such as those sold under the trademark TORX, or the like.

Figure 7:
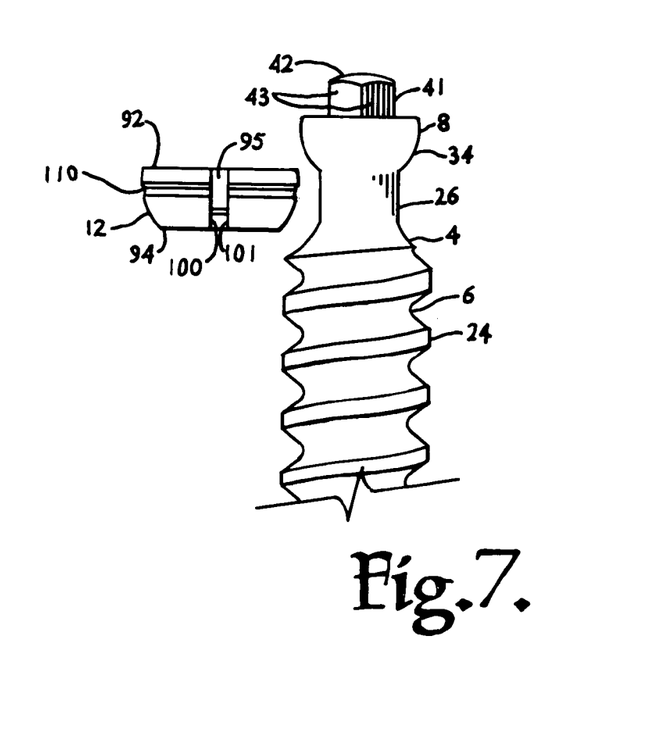
FIG. 7 is an enlarged and fragmentary front elevational view, showing the retaining and articulating structure and the bone screw shank and capture structure of FIG. 1 prior to assembly.

Prior to the polyaxial bone screw assembly 1 being placed in use according to the invention, the retaining and articulating structure 12 is first inserted about the neck 26 of the shank body 6 as illustrated in FIGS. 7 and 8, with the end surfaces 100 and 101 being pulled away from one another and pressed against and about the neck 26 until the surfaces 100 and 101 expand around the neck 26 and then spring back into a first position with the inner surface 95 disposed adjacent to the neck 26 and the top surface 92 facing toward the spherical surface 34 of the capture structure 8. The capture structure 8 and the connected structure 12 are then simultaneously up or bottom-loaded into the receiver cavity 78 as shown in FIG. 9, by inserting the capture structure into the cavity 78 and manually compressing the structure 12 by pinching the surfaces 100 and 101 toward one another and inserting the neck 26 and the compressed structure 12 into the bore 84 that opens to the lower exterior surface 86 of the receiver 10. After the retaining and articulating structure 12 moves beyond the bore 84 and into the cavity 78, the compressive force is removed and the structure 12 resiliently springs back and returns to the original ring-like or collar-like orientation. Then, as illustrated in FIG. 10, the top surface 92 of the structure 12 is pressed against the upper surface 88 of the relief 87 within the receiver 10 and the shank 4 is pulled or pressed in an opposite downward direction toward the receiver base 50, forcing the structure 12 to temporarily expand about the spherical surface of the capture structure 8 with the end surfaces 100 and 101 moving away from one another. Such an expansion of the structure 12 allows the capture structure 8 spherical surface 34 to slide into the retaining and articulating structure 12 until the outer radius of the capture structure 8 is in cooperation with the inner radius of the retaining and articulating structure 12 such that the structures 8 and 12 are in sliding pivotal relationship. The structure 12 resiliently returns to the original ring-link orientation, with the spherical surface 95 capturing the capture structure 8 at the spherical surface 34, but allowing for pivotal, sliding movement or articulation of the structure 12 with respect to the capture structure 8. Once the structure 12 returns to the original orientation, both the connected structures 8 and 12 drop down to a seated position with the structure 12 independently slidable with respect to both the structure 8 and the receiver 10, forming a multi- or compound articulation or joint between the shank 4 and the receiver 10. The structure 12 is seated in sliding engagement with the seating surface 82 of the receiver 10, with the shank 4 in slidable and rotatable engagement with the retaining and articulating structure 12 and the structure 12 in slidable rotatable engagement with the receiver 10, while the lower aperture or neck 83 of the receiver 10 cooperates with the capture structure 8 and the retaining and articulating structure 12 to maintain the shank body 6 within the receiver 10.

It is foreseen that in certain smaller embodiments, the retaining and articulating structure 12 may be down or top-loaded into the receiver U-shaped channel 56, utilizing some compression if necessary, and then temporarily expanded to surround a convex capture structure of a bone screw shank disposed within a receiver cavity as previously described herein. It is also foreseen that the bone screw shank may be top loadable.

The retaining and articulating structure 12 and attached capture structure 8 may then be manipulated into a substantially coaxial position in readiness for bone implantation. The assembly 1 is typically screwed into a bone, such as the vertebra 15, by rotation of the shank 4 using a driving tool (not shown) that operably drives and rotates the shank 4 by engagement thereof with the faces 43 of the hexagonally shaped tool engagement structure 41 of the shank 4. Preferably, when the driving tool engages the structure 41, a bottom or end portion thereof abuts the countersunk planar base 40 and outer surfaces of the driving tool engage the walls that define the outer perimeter 44, providing an additional driving interface.

Typically, the receiver 10 and the retaining and articulating structure 12 are assembled on the shank 4 before inserting the shank body 6 into the vertebra 15 as previously described hereon. However, in certain circumstances, such as when a small bone screw is utilized and the retaining and articulating structure is top loadable, the shank body 6 can be first partially implanted with the capture structure 8 extending proud to allow assembly with the receiver 10, followed by assembly with the top loaded retaining and articulating structure 12 within the receiver. Then the shank body 6 can be further driven into the vertebra 15.

The vertebra 15 may be pre-drilled to minimize stressing the bone and have a guide wire (not shown) inserted to provide a guide for the placement and angle of the shank 4 with respect to the vertebra 15. A further tap hole may be made using a tap with the guide wire as a guide. Then, the assembly 1 or the solitary shank 4, is threaded onto the guide wire utilizing the cannulation bore 45 by first threading the wire into the bottom opening 46 and then out of the top opening 48. The shank 4 is then driven into the vertebra 15, using the wire as a placement guide.

With reference to FIGS. 11 and 12, the rod 21 is eventually positioned within the receiver U-shaped channel 56, and the closure structure or top 18 is then inserted into and advanced between the arms 52 and 54 so as to bias or push against the rod 21. The break-off head 130 of the closure structure 18 is twisted to a preselected torque, for example 90 to 120 inch pounds, to urge the rod 21 downwardly. The shank top end surface 42, because it is rounded to approximately equally extend upward into the channel 56 approximately the same amount no matter what degree of rotation exists between the shank 4 and receiver 10 and because the surface 42 is sized to extend upwardly into the U-shaped channel 56, the surface 42 is engaged by the rod 21 and pushed downwardly toward the base 50 of the receiver 10 when the closure structure 18 biases downwardly toward and onto the rod 21. The downward pressure on the shank 4 in turn urges the retaining and articulating structure 12 downward toward the receiver seating surface 82, with the retaining and articulating structure seating surface 104 in further frictional engagement with the receiver seating surface 82 and the capture structure 8 spherical surface 34 in further frictional engagement with the retaining and articulating structure inner spherical surface 95. As the closure structure 18 presses against the rod 21, the rod 21 presses against the shank and the retaining and articulating structure 12 becomes frictionally and rigidly attached to the shank 4 which in turn becomes frictionally and rigidly attached to the receiver 10, fixing the shank body 6 in a desired angular configuration with respect to the receiver 10 and the rod 21.

FIG. 11 illustrates the polyaxial bone screw assembly 1 and including the rod 21 and the closure structure 18 positioned in a vertebra 15 at a level or extent of ball-and-socket or spheroidal articulation in which the axis C of the retaining and articulating structure 12 is coaxial with the axis B of the receiver and the axis A of the bone shank 4 is at an angle with respect to the axis B of the receiver 10, with the shank 4 being fixed in this angular locked configuration. FIG. 12 illustrates a further level or extent of angular orientation or articulation possible with a bone screw assembly of the invention wherein the axes A, B, and C are not coaxial, allowing for an increased range or extent of rotation or articulation of the bone screw shank 6 with respect to the receiver 10 utilizing two universal or ball joints. Thus, according to the invention, a compound spheroidal articulation is possible, taking advantage of a full range of angular positions due to the ball-and-socket joint formed between the shank capture structure 8 and the retaining and articulating structure 12 and also the ball-and-socket joint between the retaining and articulating structure 12 and the receiver 10, allowing for a full range of rotation, both from side to side and front to rear. Thus, in addition to those shown in FIGS. 11 and 12, a variety of other angular configurations can be achieved, as required during installation surgery due to positioning of the rod 21 or the like. It is foreseen that the compound articulation of the present invention may also be formed between convex and concave surfaces that are not spheroidal. For example, elliptical convex surfaces and/or conical concave surfaces may be utilized in addition to the spheroidal mating surfaces illustrated herein.

If removal of the assembly 1 and the associated rod 21 and the closure structure 18 is necessary, disassembly is accomplished by using a driving tool (not shown) mating with an aperture or other driving surface on the closure structure 18 to rotate the base 138 and reverse the advancement thereof in the receiver 10. Then, disassembly of the assembly 1 is accomplished in reverse order to the procedure described previously herein for assembly.

It is to be understood that while certain forms of the present invention have been illustrated and described herein, it is not to be limited to the specific forms or arrangement of parts described and shown.

The invention claimed is:

1. A polyaxial bone screw assembly comprising:
   a) a bone screw shank having an upper portion with a first engagement surface;
   b) a receiver having a cavity with a second engagement surface, the bone screw upper portion receivable in the cavity;
   c) a retaining and articulating structure receivable in the cavity between the shank upper portion and the receiver; the retaining and articulating structure having a third engagement surface operably mating with the shank first engagement surface and a fourth engagement surface operably mating with the receiver second engagement surface; the retaining and articulation structure being pivotal with respect to both the shank and the receiver so as to be able to freely move relative to both the shank and the receiver during positioning of the shank relative to the receiver;

d) a first polyaxial articulation formed by the first engagement surface of the upper portion and the third engagement surface of the retaining and articulating structure; and e) a second polyaxial articulation formed by the fourth engagement surface of the retaining and articulating structure and the second engagement surface of the receiver whereby during positioning of the shank relative to the receiver compound articulation exists between the shank and the receiver.

2. The assembly of claim 1 wherein the shank upper portion has a convex surface and the retaining and articulating structure has a concave surface in slidable mating engagement with the convex surface.

3. The assembly of claim 2 wherein at least one of the convex surface and the concave surface is a roughened surface.

4. The assembly of claim 1 wherein the retaining and articulating structure has a convex surface and the receiver has a concave surface in slidable mating engagement with the convex surface.

5. The assembly of claim 4 wherein at least one of the convex surface and the concave surface is a roughened surface.

6. The assembly of claim 1 wherein the first polyaxial articulation is spheroidal.

7. The assembly of claim 1 wherein the second polyaxial articulation is spheroidal.

8. The assembly of claim 1 wherein the shank upper portion has a tool engagement formation disposed thereon adapted for non-slip engagement by a tool for driving the bone screw shank into bone.

9. The assembly of claim S wherein the tool engagement formation is an axial projection having a hexagonal profile.

10. The assembly of claim 1 wherein the retaining and articulating structure further comprises first and second spaced ends, the retaining and articulating structure being compressible and expandable with the first and second ends being movable toward and away from one another.

11. The assembly of claim 1 wherein the retaining and articulating structure is sized and shaped to be at least one of top-loadable and bottom-loadable into the receiver.

12. The assembly of claim 1 wherein the bone screw shank has a body for fixation to bone, the shank body being integral with the shank upper portion.

13. The assembly of claim 12 wherein the bone screw shank is cannulated.

14. The assembly of claim 12 further comprising a closure structure insertable into the receiver, the closure structure for operably urging the bone screw shank in a direction to frictionally lock the position of the retaining and articulating structure with respect to the shank upper portion and the receiver, thereby locking the shank body in a selected angle with respect to the receiver.

15. The assembly of claim 14 wherein:

(a) the receiver has upstanding spaced arms defining an open channel, the arms having guide and advancement structures on an inside surface thereof; and (b) the closure structure is sized and shaped to be positionable between the arms for closing the channel, the closure structure having a closure guide and advancement structure for rotatably mating with the guide and advancement structures on the arms, biasing the closure structure upon advancement rotation against a rod disposed in the channel.

16. The assembly of claim 15 wherein the shank upper portion has a dome sized and shaped to extend into the channel for engagement with a rod when received in the receiver and wherein the closure structure is adapted to operably urge the rod against the dome upon the closure structure being positioned in the receiver.

17. The assembly of claim 1 wherein the receiver defines a relief and the retaining and articulating structure defines a groove for expansion of the retaining and articulating structure within the receiver cavity.

18. A polyaxial bone screw assembly comprising:

a) a shank having an upper portion with a first convex partially spherical articulation surface and a body for fixation to bone;

b) a receiver with a first concave partially spherical articulation surface for receiving the shank upper portion;

c) an articulation structure for retaining the shank upper portion in the receiver that is located between and is unattached to both the shank and the receiver; the articulation structure having a second convex partially spherical articulation surface and a second concave partially spherical articulation surface; whereby d) a compound articulation is formed by the shank upper portion, the articulation structure and the receiver wherein the articulation structure second convex partially spherical surface is articulably received on the receiver first convex partially spherical surface and the shank first convex articulation structure is articulably received on the articulation structure second partially spherical concave surface; such that the shank upper portion articulation structure articulates with the articulation structure and the articulation structure also articulates with the receiver during positioning of the shank relative to the receiver.

19. The assembly of claim 18 wherein:

a) the articulation structure cooperates with the shank and the receiver for retaining the shank upper portion in the receiver has a first convex surface; the articulation structure is located between the shank and the receiver;

b) the articulating structure has a first concave seating surface and a second convex surface, the first concave seating surface configured for slidable mating engagement with the first convex surface; and c) the receiver has a second concave seating surface configured for slidable mating engagement with the second convex surface, so as to provide compound articulation between the shank and the receiver during positioning.

20. The assembly of claim 19 wherein the first and second convex surfaces are both substantially spherical.

21. The assembly of claim 19 wherein the first and second concave surfaces are substantially spherical.

* * * * *